US00PP24375P3

(12) United States Plant Patent
Harris

(10) Patent No.: US PP24,375 P3
(45) Date of Patent: Apr. 8, 2014

(54) AZALEA PLANT NAMED 'MNIHAR024'

(50) Latin Name: ***Rhododendron* sp.**
Varietal Denomination: MNIHAR024

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 50 days.

(21) Appl. No.: 13/573,109

(22) Filed: Aug. 22, 2012

(65) Prior Publication Data

US 2014/0059726 P1 Feb. 27, 2014

(51) Int. Cl.
*A01H 5/00* (2006.01)

(52) U.S. Cl.
USPC ..... Plt./238

(58) Field of Classification Search
USPC ..... Plt./238
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of azalea plant with spring and fall blooming, attractive, showy, single to semi-double orange-red flowers, easily propagated by semi-hardwood cuttings in late spring through summer, moderate growth rate under normal fertilization and moisture conditions; compact, broadly-globose and freely-branching growth habit, grows well in containers, thrives in shade or sun and is hardy to Zone 7, is disclosed.

2 Drawing Sheets

Genus and species: *Rhododendron* sp.
Variety denomination: 'MNIHAR024'.

BACKGROUND OF THE NEW PLANT

The present invention is a new and distinct variety of evergreen azalea in the genus *Rhododendron*. This new azalea, hereinafter referred to as 'MNIHAR024', originated from a planned cross hybridization in 2001 between the female azalea plant 'Maria Derby' (unpatented) and the male azalea plant 'Conleb' (U.S. Plant Pat. No. 10,581) in a controlled environment in Lawrenceville, Ga. The present invention has a blooming period of late March to mid April and early August until frost. 'MNIHAR024' has a compact, broadly globose freely branching growth habit, and cold hardiness.

The new plant was first propagated via semi-hardwood cuttings in 2005 in Dearing, Ga. and has been asexually reproduced repeatedly by semi-hardwood cuttings in Dearing, Ga. for over 5 years, four generations. 'MNIHAR024' has been found to retain its distinctive characteristics through successive asexual propagations via semi-hardwood cuttings.

Plant Breeder's Rights for this variety have not been applied for. 'MNIHAR024' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, orange-red colored flowers;
3. Numerous single to semi-double flowers;
4. Easily propagated by semi-hardwood cuttings in late spring through summer;
5. Moderate growth rate under normal fertilization and moisture conditions;

6. Compact, broadly globose freely branching growth habit;
7. Grows well in containers;
8. Thrives in shade or sun; and
9. Hardy in Zone 7.

DESCRIPTION OF THE PHOTOGRAPHS

This new azalea hybrid variety is illustrated by the accompanying photographs. The colors shown are as true as can be reasonably obtained by conventional photographic means. The photographs are of five-year-old plants grown in filtered shade and three-year-old plants grown in full sun in 2010 and 2011 in Dearing, Ga.

DETAILED BOTANICAL DESCRIPTION OF THE NEW PLANT

Figure 1:
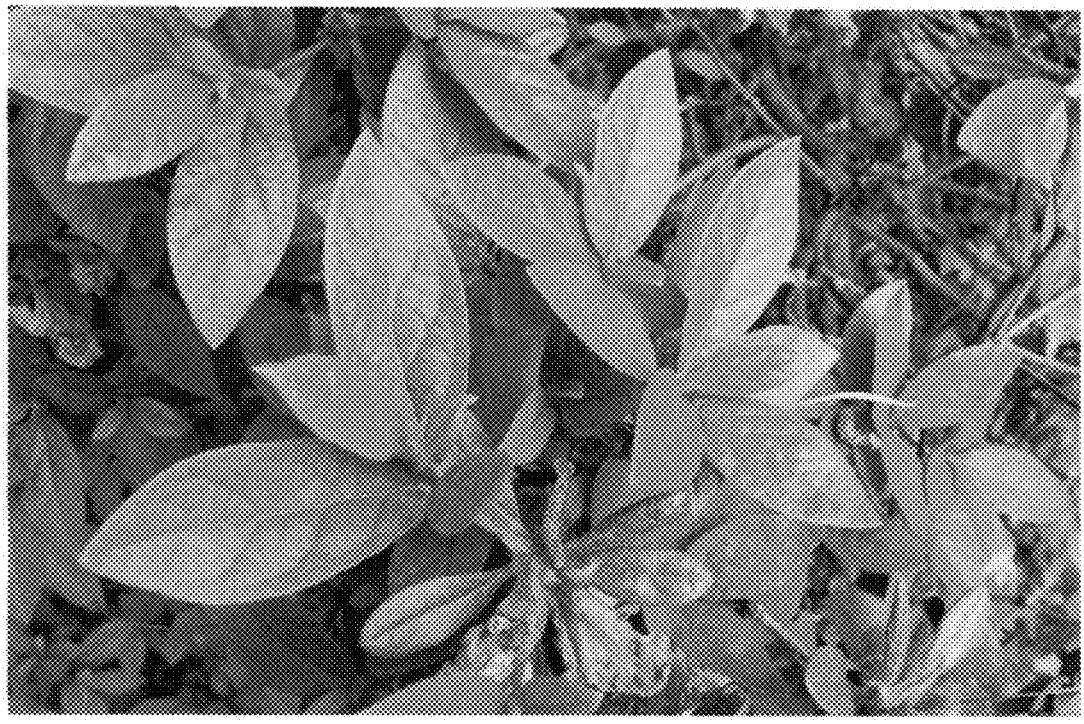
FIG. 1 is a close-up showing immature foliage.
Figure 2:
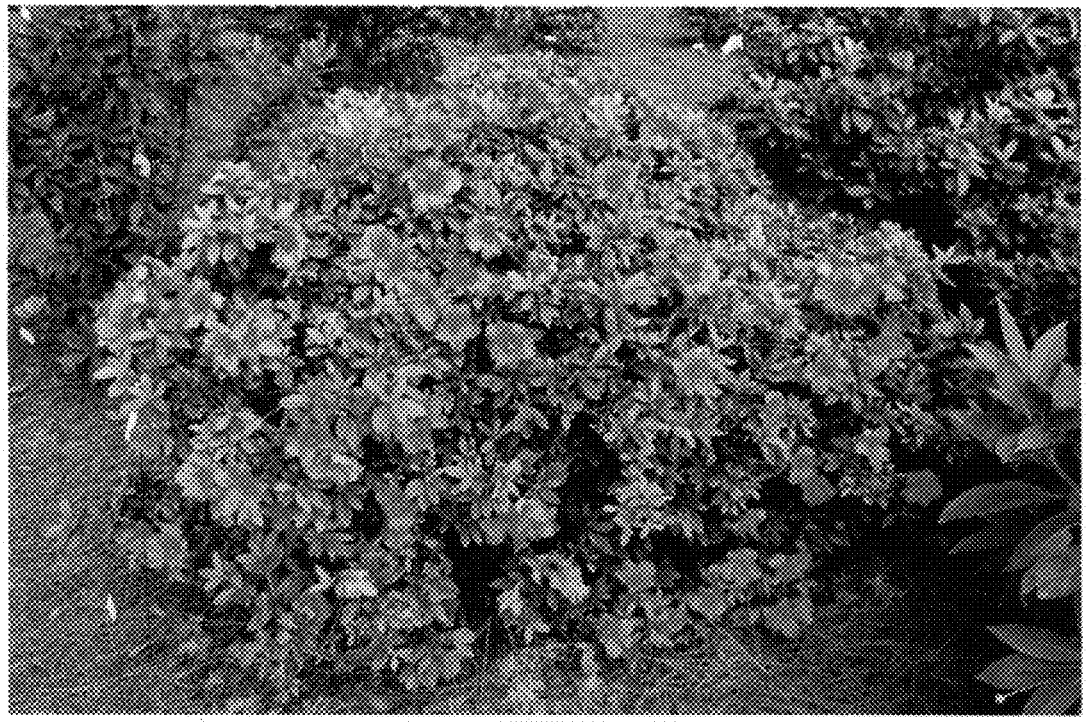
FIG. 2 shows growth habit and fall flowering.
Figure 3:
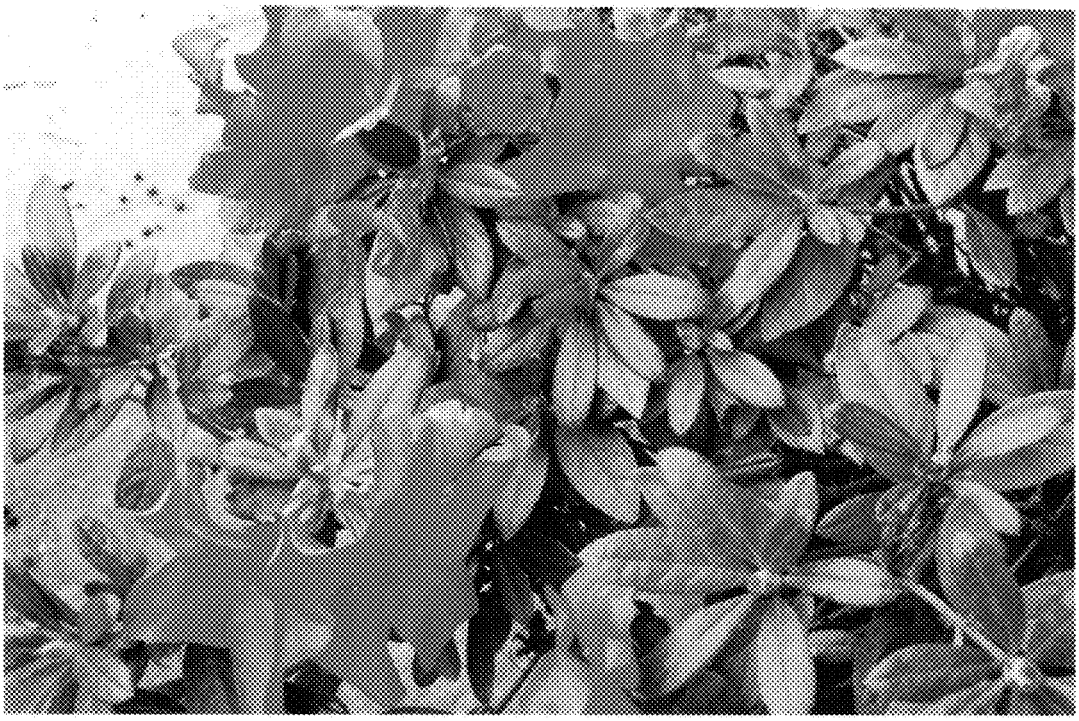
FIG. 3 is a close-up showing mature foliage and flower buds.
Figure 4:
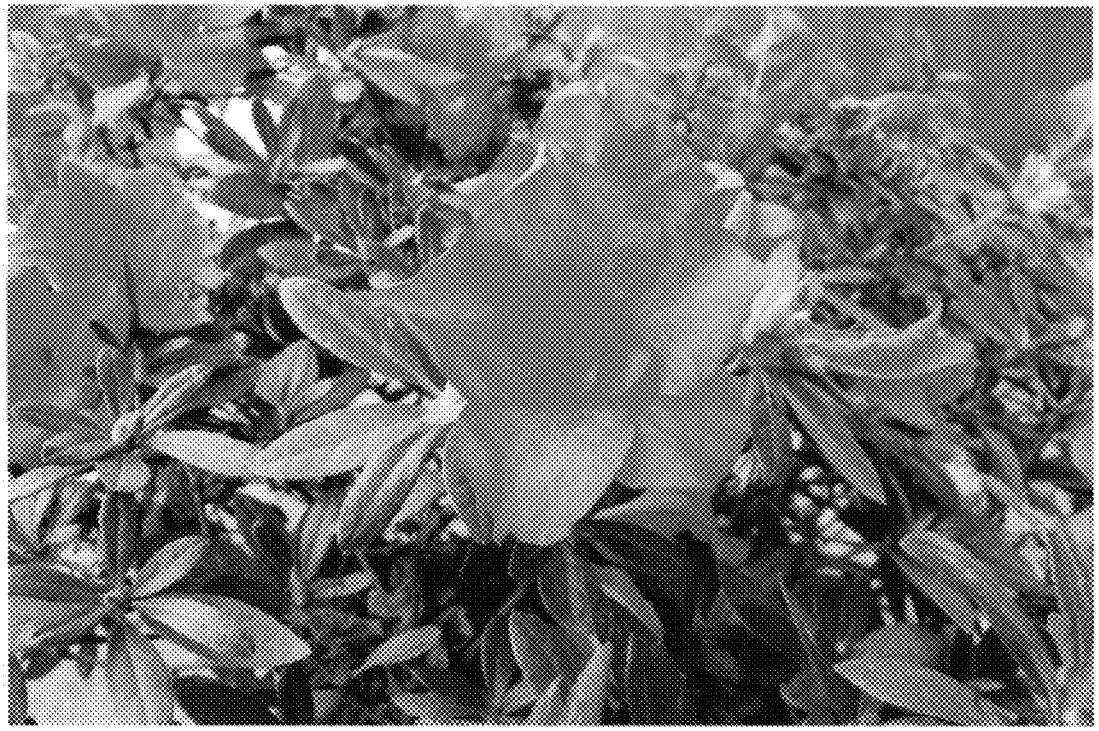
FIG. 4 is a close-up showing flower size, form, and color.

The following is a detailed description of the new variety of azalea based on observations made of two and three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, 2010, 2011, and 2012. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Denomination*.—'MNIHAR024'.

Parentage:

*Female parent*.—The azalea plant 'Maria Derby' (unpatented).

*Male parent*.—The azalea plant 'Conleb' (U.S. Plant Pat. No. 10,581).

Plant:

*Form*.—Compact, broadly globose.

*Texture*.—Medium.

*Height* (*at maturity*).—91.44 cm to 121.92 cm.

*Width* (*at maturity*).—152.4 cm to 182.88 cm.

*Growth habit*.—Freely branching; compact broadly globose.

*Growth rate*.—Moderate growth rate under normal fertilization and moisture conditions. In a period of 5 years from a rooted cutting the plant reaches a height of 84.0 cm and a spread of 127.0 cm. The growth rate averages about 13.0 cm per year; the plant reaches a height of 91.44 cm to 121.92 cm at maturity while maintaining a compact broadly globose habit due to the abundant deliquescent branch development.

*Spring growth*.—The date of initial spring growth is March 20, followed by continuous growth through fall.

*Life cycle*.—Perennial evergreen.

Leaves:

*Arrangement*.—Alternate, simple, pubescent, and evergreen.

*Shape*.—Elliptic to oblanceolate.

*Apex*.—Mucronate.

*Base*.—Attenuate.

*Margin*.—Entire.

*Length*.—3.5 cm.

*Width*.—1.4 cm.

*Venation pattern*.—Pinnate; the mid-veins and laterals are impressed on the upper surface and the prominent on the lower surface.

*Immature leaf*.—Upper surface: Color: Semi-glossy to matte, RHS 144A (yellow-green). Pubescence: Strigose and scabrous. Pubescence color: RHS 165C (greyed-orange). Lower surface: Color: Semi-glossy to matte, RHS 146C (yellow-green). Pubescence: Strigose and scabrous. Pubescence color: RHS 165C (greyed-orange).

*Mature leaf*.—Upper surface: Color: Matte, RHS 147A (yellow-green). Pubescence: Strigose and scabrous, low amount. Color: RHS 155C (white). Lower surface: Color: Matte to semi-glossy, RHS 147B (yellow-green). Pubescence: Strigose and scabrous, moderate amount. Pubescence color: RHS 164B (greyed-orange).

*Petiole*.—Length: 0.8 cm. Diameter: 0.1 cm to 0.15 cm. Pubescence: Strigose. Length: 0.16 cm. Color: RHS N167C (greyed-orange). Color: RHS 144A (yellow-green).

Stems:

*Form*.—Branched at terminal buds with some from auxiliary buds at leaf nodes.

*Young stems* (*actively growing, less than one year old*).—Color: RHS N79A (purple) and RHS 144B (yellow-green) maturing to RH 165A (greyed-orange). Pubescence: Strigose. Pubescence color: RHS 165B (greyed-orange). Length of fully elongated flush: 6.6 cm on average. Diameter: 0.2 cm.

*Mature stems* (*one year old and older*).—Color: RHS 197B (greyed-green) and RHS 166A (greyed-orange). Pubescence: Strigose, RHS 166A (greyed-orange), decreasing amount with age. Length: 14.0 cm on average for full year's growth. Diameter: 0.3 cm in second year. Pith: Solid and uniform. Internode length: Average 1.25 cm on actively growing vegetative stems.

Flower buds:

*Arrangement and form* (*at terminal end*).—Borne in groups of two or three, sheathed by zero, one, two, or three modified leaf bracts.

*Bracts*.—Length: Average 1.8 cm. Width: 0.4 cm. Color: RHS 147A (yellow-green).

*Shape*.—Ovate.

*Apex*.—Acute.

*Base*.—Rounded.

*Length* (*at tight bud*).—1.2 cm.

*Diameter* (*at tight bud*).—0.8 cm.

*Scales*.—Color: Immature: RHS 145C (yellow-green). Mature: RHS 144A (yellow-green) with areas of N34A (orange-red). Texture: Matte, strigose pubescence mainly at the bud scale midrib. Pubescence color: RHS 167C (greyed-orange).

*Pedicel*.—Length: 0.7 cm when bud begins to open. Diameter: 0.15 cm. Texture: Pubescent, strigose and villous pubescence. Pubescence color: RHS N155A (white) with RHS 168D (greyed-orange) at the base. Color: RHS 46A (red).

Calyx:

*Calyx diameter*.—0.9 cm from sepal apex to sepal apex.

*Texture*.—Pubescent, villous pubescence. Pubescence color: RHS N155A (white).

*Color*.—RHS 144B (yellow-green).

*Sepals*.—Quantity: 5. Length: 0.6 cm. Diameter: 0.2 cm.

Flowers:

*Type*.—Perfect, single to semi-double flowers.

*Shape*.—Open funnel-shaped.

*Flowering habit and period*.—Borne on the current season's growth; three weeks in late March to mid April in Dearing, Ga.; flowering resumes early August and continues until frost which can be as late as November or December. Lastingness of flowers on the plant 4 to 6 days in the sun; 4 to 7 days in the shade.

*Fragrance*.—Absent.

*Diameter*.—6.2 cm.

*Depth*.—3 cm.

*Petals*.—Quantity per flower and arrangement: Five imbricate petals that are fused at the base and remain fused 1.5 cm to 2.2 cm from the base. Shape: Obovate. Apex: Retuse. Base: Fused. Margin: Entire, slightly undulate. Texture (both upper and lower surfaces): Glabrous. Length (petals without spots): 4 cm. Length (petals with spots): 4.5 cm. Width (petals without spots): 3 cm. Width (petals with spots): 2.8 cm. Color: Upper surface: RHS 50B (red), spots on the upper surface of the petal are RHS 53A (red). Lower surface: RHS 48A (red), spots on the lower surface of the petal are not visible.

Reproductive parts:

*Pistil*.—Quantity and form: Single, non-petaloid. Length: 4.8 cm. Diameter: 0.075 cm.

*Stigma*.—Color: RHS 46A (red). Diameter: 0.15 cm.

*Style color*.—RHS 46A (red).

*Ovary*.—Pilose pubescence, RHS N155A (white) with 5 locules.

*Ovary color*.—RHS 141A (green).

*Stamens*.—Quantity: 5 per flower; petaloid and non-petaloid. Length: Non-petaloid average 2.7 cm, petaloid up to 3.5 cm in length. Width: Up to 3.0 cm for petaloid stamens. Color: RHS 47C (red).

*Anther*.—Length: 0.2 cm. Width: 0.1 cm. Color: RHS 164B (greyed-orange). Pollen: Abundant. Color: RHS 155D (white).

Fruit and seed: Observed.

*Maturity*.—The capsule matures in about 6 months in Dearing, Ga. and the fruit set is moderate and contains about 100 to 200 non-winged seeds.

*Capsule*.—Length: 0.9 cm. Width: 0.5 cm. Color: RHS 146A (yellow-green).

CULTURE

'MNIHAR024' grows well in a wide range of conditions and tolerates sun to shade. 'MNIHAR024' prefers moist, well-drained soil that is rich in organic matter and responds well to mulching and medium applications of fertilizer. 'MNIHAR024' does best in soil with a pH of 5.0 to 5.5 and is propagated with semi-hardwood cuttings in late spring through the summer. 'MNIHAR024' roots in five to six weeks with a high percentage of rooting (80% plus). Tissue culture is also an effective means of propagation of 'MNIHAR024'.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR024' is compared to parental varieties 'Maria Derby' (unpatented) and 'Conleb' (U.S. Plant Pat. No. 10,581).

TABLE 1

| Characteristic | 'MNIHAR024' | 'Maria Derby' | 'Conleb' |
|---|---|---|---|
| Plant Height (Mature) | 91.44 cm to 121.92 cm | 91.44 cm to 121.92 cm | 121.92 cm to 152.4 cm |
| Flower Diameter | 6.2 cm | 6.35 cm | 6.5 cm |
| Flower Form | Single to Semi-double | Double to hose-in-hose | Single to semi-double |
| Flower Color | Orange-red | Deep reddish orange | Red |
| Bloom Period | Late March to Mid April and early August until frost | May | April and late July until frost |
| Hardy Zone | 7 | 6b | 7 |
| Stamen Number | 5 | 0 to 5 | 0 to 9 |
| Stamen Type | Petaloid and non-petaloid | Petaloid and non-petaloid | Petaloid and non-petaloid |

When 'MNIHAR024' is compared to the commercial variety 'Roblen' (U.S. Plant Pat. No. 16,248), 'MNIHAR024' has a compact broadly globose growth habit with a height of 84.0 cm and a spread of 127.0 cm in 5 years, while 'Roblen' has a height of 91.44 cm and a spread of 60.96 cm in six years. Additionally, 'MNIHAR024' has flowers with petals colored RHS 50B (red) on the upper surface and RHS 48A (red) on the lower surface, whereas 'Roblen' has flowers with petals colored RHS 44C (red).

I claim:

1. A new variety of azalea plant named 'MNIHAR024' as herein shown and described.

* * * * *